US009254246B2

(12) United States Patent
Klee et al.

(10) Patent No.: US 9,254,246 B2
(45) Date of Patent: Feb. 9, 2016

(54) SELF-DENTAL ADHESIVE COMPOSITION

(75) Inventors: Joachim Klee, Radolzfell (DE); Uwe Lehmann, Constance (DE); Anja Glaner, Constance (DE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/462,609

(22) Filed: Aug. 6, 2009

(65) Prior Publication Data

US 2010/0130637 A1 May 27, 2010

(30) Foreign Application Priority Data

Feb. 6, 2008 (WO) ................ PCT/EP2008/000916

(51) Int. Cl.
*A61K 6/083* (2006.01)
*A61K 6/00* (2006.01)

(52) U.S. Cl.
CPC ............. *A61K 6/0073* (2013.01); *A61K 6/0017* (2013.01); *A61K 6/083* (2013.01)

(58) Field of Classification Search
CPC ............................ A61K 6/083; A61K 6/0073
USPC ......................................................... 523/115
See application file for complete search history.

(56) References Cited

U.S. PATENT DOCUMENTS

| | | | | |
|---|---|---|---|---|
| 6,660,785 | B2 * | 12/2003 | Klee et al. | 523/116 |
| 6,756,417 | B2 * | 6/2004 | Allred et al. | 522/13 |
| 6,953,832 | B2 | 10/2005 | Moszner et al. | |
| 2006/0135719 | A1 * | 6/2006 | Moszner et al. | 526/303.1 |
| 2006/0246017 | A1 * | 11/2006 | Klee et al. | 424/57 |

FOREIGN PATENT DOCUMENTS

| | | | |
|---|---|---|---|
| EP | 0 335 645 | 8/1992 | |
| EP | 0 621 028 | 10/1994 | |
| EP | 1911434 A1 * | 4/2008 | A61K 6/00 |
| WO | WO 02/13768 | 2/2002 | |
| WO | WO 03/013444 | 2/2003 | |
| WO | WO 03/035013 | 5/2003 | |
| WO | WO 2004/078100 | 9/2004 | |
| WO | WO 2005/063778 | 7/2005 | |
| WO | WO 2005063778 A1 * | 7/2005 | |
| WO | WO 2008/095694 | 8/2008 | |

* cited by examiner

*Primary Examiner* — Michael Pepitone
(74) *Attorney, Agent, or Firm* — Douglas J. Hura; Leana Levin; David A. Zdurne

(57) ABSTRACT

Self-adhesive dental restorative composition comprising (i) 10 to 40 percent by weight based on the total weight of the composition of a mixture of hydrolysis-stable polymerizable monomers of the following formula (I): wherein R is a m+n valent organic group having 1 to 20 carbon atoms and optionally 1 to 5 atoms selected from the group of nitrogen, oxygen and sulfur atoms; A independently represents a moiety of the following formula (II): wherein L is a hydrogen atom, a C1-6 alkyl group, a C3-8 cycloalkyl group, a C6-14 aryl group or a group of the following formula (III) wherein R' is a hydrogen atom, a C1-6 alkyl group, a C3-8 cycloalkyl group, or a C6-14 aryl group; X is O, S, NH or NR" wherein R" is a C1-6 alkyl group, a C3-8 cycloalkyl group, a C6-14 aryl group; a is 0 or 1; M is a group of the following formula (IV) wherein Y is O, S, NH or NR'" wherein R'" is a C1-6 alkyl group, a C3-8 cycloalkyl group, a C6-14 aryl group; b is an integer of from O to 3; c is O or 1; d is an integer of from O to 3; provided that when b is O, then Y cannot be O; x is 0 or 1; y is 0 or 1; provided that x and y cannot be both 1, and provided that x cannot be 1 when L or a group of formula (III) is a hydrogen atom, and provided that when x is 0 then a is also 0, and provided that when y is 0 then b is greater than 0 or c is 0; B independently represents an acidic group; m is an integer of from 1 to 5; n is an integer of 0 to 3; and m+n is at least 2; (ii) 60 to 90 percent by weight based on the total weight of the composition of a filler; and (iii) an initiator system; wherein the portion of monomers of formula (I) wherein n is greater than 0 is at least 1 percent by weight based on the total weight of the mixture.

17 Claims, No Drawings

SELF-DENTAL ADHESIVE COMPOSITION

The present invention relates to a self-adhesive dental restorative composition providing high mechanical resistance over the entire lifetime of the dental restoration after curing. The dental restorative composition may be a self-adhesive dental composite, a filler containing self-adhesive sealer or a self-adhesive cement. The dental restorative composition of the present may be a one-part composition having high storage stability prior to curing and high adhesive strength to dentine and long term mechanical resistance after curing. The present invention also relates to a process for the preparation of the dental restorative composition, in particular a self-adhesive dental composite.

BACKGROUND OF THE INVENTION

Dental adhesives containing a filler are known. EP-A 0 335 645 discloses an adhesive composition comprising a monomer mixture containing a vinyl monomer having an acidic group in the molecule and a vinyl monomer copolymerizable with said vinylmonomer, a filler, and a self-curing initiator system. The adhesive composition of EP-A 0 335 645 is handled and stored as a two-pack system. Namely, liquid components and powder components are independently filled in two different packs, and at the curing and bonding step, necessary amounts of the liquid and powder components are taken out from the packs and they are kneaded together. The adhesion strength to dentine obtained are less than 1.9 MPa.

Dental materials based on polyfunctional amides are known from U.S. Pat. No. 6,953,832 which contain specific polymerizable amides and optionally strongly acidic polymerizable monomers such as dipentaerythritol pentamethacryloyloxy dihydrogenphosphate. Filler containing compositions are suggested. However, U.S. Pat. No. 6,953,832 does not disclose a self-adhesive composite.

Dental composites are used to replace natural tooth material. Accordingly, dental composite materials are required to provide a high mechanical resistance over the entire lifetime of the dental restoration after curing. In order to provide mechanical strength and for reducing polymerization shrinkage of the composite, dental composites contain a large amount of filler. Due to the large amount of filler, the viscosity of the uncured composite is usually high and adhesion of the cured composite to dentine is low. Due to the high viscosity, a highly filled dental composite can usually not be provided as a two-pack composition because reliable homogeneous mixing of the packs would be problematic prior to the application of the composite.

Moreover, an increase of the adhesive properties of the composite by incorporating acidic adhesive monomers into the composite deteriorates the shelf life of a one-pack composite prior to curing due to the hydrolysis of polymerizable monomers by acidic group containing components. Moreover, after curing, acidic groups will remain in the bulk of the cured composite so that the acidity is present throughout the lifetime of the cured composite restoration representing a continuing potential for activation of hydrolyzable groups.

In order to avoid the formation of a marginal gap by providing an adhesive bond between the cured composite and the tooth, composites are usually applied to a dental surface treated with a bonding agent, such as a dental adhesive. The application of a dental adhesive represents an additional step requiring additional time and representing a source for problems due to an additional interface between the adhesive and the composite.

SUMMARY OF THE INVENTION

Accordingly, it is the problem of the present invention to provide a self-adhesive dental restorative composition such as a self-adhesive dental composite, a filler containing self-adhesive sealer or a self-adhesive cement, having excellent storage stability and long term mechanical resistance, whereby the self-adhesive dental restorative composition may be applied directly on the dental surface as a one-pack composition without prior application of a bonding agent.

Accordingly, the present invention provides a self-adhesive dental restorative composition, in particular a self-adhesive dental composite comprising:

(i) 10 to 40 percent by weight based on the total weight of the composition of a mixture of hydrolysis-stable polymerizable monomers of the following formula (I):

$$R(A)_m(B)_n \quad (I)$$

wherein

R is a m+n valent organic group having 1 to 20 carbon atoms and optionally 1 to 5 atoms selected from the group of nitrogen, oxygen and sulfur atoms; independently represents a moiety of the following formula (II):

(II)

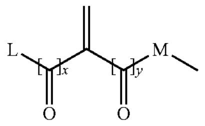

wherein

L is a hydrogen atom, a C1-6 alkyl group, a C3-8 cycloalkyl group, a C6-14 aryl group or a group of the following formula (III):

(III)

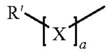

wherein

R' is a hydrogen atom, a C1-6 alkyl group, a C3.8 cycloalkyl group, or a C6-14 aryl group; X is O, S, NH or NR" wherein R" is a C1-6 alkyl group, a C3ˆ8 cycloalkyl group, a C6-14 aryl group; a is 0 or 1;

M is a group of the following formula (IV)

(IV)

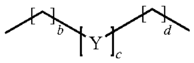

wherein

Y is O, S, NH or NR'" wherein R'" is a C1-6 alkyl group, a C3.8 cycloalkyl group, a C6-14 group; b is an integer of from O to 3; c is O or 1; d is an integer of from O to 3; provided that when b is 0, then Y cannot be O; x is O or i; y is O or 1; provided that x and y cannot be both 1, and provided that x cannot be 1 when L or a group of formula (III) is a hydrogen atom, and provided that when x is 0 then a is also 0, and provided that when y is 0 then b is greater than 0 or c is 0; B independently represents an acidic group; m is an integer of from 1 to 5; n is an integer of 0 to 3; and m+n is at least 2; (ii) 60 to 90 percent by weight based on the total weight of the composition of a filler; and (iii) an initiator system; wherein the portion of monomers of formula (I) wherein n is greater than 0 is at least 1 percent by weight based on the total weight of the mixture.

Moreover, the present invention relates to a process for the preparation of a self-adhesive dental restorative composition, in particular a dental composite, which comprises the step of mixing:

(i) 10 to 40 percent by weight based on the total weight of the composition of a mixture of hydrolysis-stable polymerizable monomers of the following formula (I):

$$R(A)_m(B)^n \quad (I)$$

wherein

R is a m+n valent organic group having 1 to 20 carbon atoms and optionally 1 to 5 atoms selected from the group of nitrogen, oxygen and sulfur atoms; A independently represents a moiety of the following formula (II):

(II)

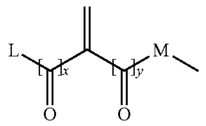

wherein

L is a hydrogen atom, a C1-6 alkyl group, a C3-8 cycloalkyl group, a C6-14 aryl group or a group of the following formula (III):

(III)

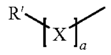

wherein

R' is a hydrogen atom, a C1-6 alkyl group, a C3.8 cycloalkyl group, or a C6-14 aryl group; X is O, S, NH or NR" wherein R" is a C1-6 alkyl group, a C3-8 cycloalkyl group, a C6-14 aryl group; a is 0 or 1;

M is a group of the following formula (IV)

(IV)

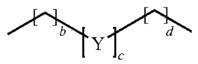

wherein

Y is O, S, NH or NR'" wherein R'" is a C1-6 alkyl group, a C3.8 cycloalkyl group, a C6-14 aryl group; b is an integer of from O to 3; c is O or 1; d is an integer of from O to 3; provided that when b is O, then Y cannot be O; x is O or 1; y is O or 1; provided that x and y cannot be both 1, and provided that x cannot be 1 when L or a group of formula (III) is a hydrogen atom, and provided that when x is O then a is also O, and provided that when y is 0 then b is greater than O or c is 0;

B independently represents an acidic group; m is an integer of from 1 to 5; n is an integer of 0 to 3; and m+n is at least 2;

(ii) 60 to 90 percent by weight based on the total weight of the composition of a filler; and (iii) an initiator system; wherein the portion of monomers of formula (I) wherein n is greater than 0 is at least 1 percent by weight based on the total weight of the mixture.

DETAILED DESCRIPTION OF THE PREFERRED EMBODIMENTS

The self-adhesive dental restorative composition such as a dental composite, according to the invention contains a mixture of hydrolysis-stable polymerizable monomers. The mixture contains at least an acidic polymerizable monomer. Preferably, the mixture contains at least a crosslinking polymerizable monomer and an acidic polymerizable monomer. The polymerizable monomers are hydrolysis-stable. Specifically, the polymerizable monomers do not contain groups such as ester groups, in the main chain which hydrolyze in aqueous media at pH 3 at room temperature within one month.

The polymerizable monomers are compounds of formula (I). The monomer of formula (I), comprises a moiety R, up to five polymerizable substituents A and optionally up to three acidic groups B. Accordingly, m is an integer of from 1 to 5 and n is an integer of from 0 to 3. The sum of m an n is at least 2. Accordingly, in case of a single polymerizable substituents A, the polymerizable monomer comprises an acidic group.

Moiety A is an organic group having 1 to 20 carbon atoms and optionally 1 to 5 atoms selected from the group of nitrogen, oxygen and sulfur atoms. In a preferred embodiment, R is an organic group having 1 to 6 carbon atoms. The organic group has a valency of at least two and corresponds to the total number of substituents A and B. Accordingly, R may be divalent (n=2), trivalent (n=3), tetravalent (n=4), pentavalent (n=5), or hexavalent (n=6). Preferable R is divalent or trivalent, most preferably divalent. A may be a hydrocarbon group which may be aliphatic and/or aromatic. The hydrocarbon group may be substituted by 1 to 6 C1-4 alkyl groups provided that the total amount of carbon atoms of R does not exceed 20. Specific examples of the alkyl groups are methyl, ethyl, n-propyl, i-propyl, n-butyl, i-butyl or tert.-butyl. In a preferred embodiment, the hydrocarbon group may contain 1 to 5 oxygen atoms in the hydrocarbon group in the form of aliphatic or aromatic ether bonds, keto groups, carboxylic acid groups, or hydroxyl groups. Ester groups are not preferred in moiety R in view of hydrolysis stability of the polymerizable monomer. In case of an aliphatic group, R may be a straight chain or branched chain alkylene group or a cycloalkylene group. In case of an aromatic group, R may be an arylene group or a heteroarylene group. Specifically, R may be a divalent substituted or unsubstituted C1 to C20 alkylene group, substituted or unsubstituted C6.14 arylene group, substituted or unsubstituted C3 to C20 cycloalkylene group, substituted or unsubstituted C7 to C20 arylenealkylenearylene group. Preferably, R represents a saturated aliphatic C2.20 hydrocarbon chain which may contain 2 to 4 oxygen atoms, and which may be substituted by 1 to 6 C1-4 alkyl groups, or R may be a substituted or unsubstituted C7 to C20 arylenealkylenearylene group which may be substituted by 1 to 6 C1-4 alkyl groups.

The polymerizable monomer of formula (I) contains at least one and up to five polymerizable substituents A. In case more than one A is present, each A independently represents a moiety of the following formula (II). Accordingly, in one embodiment all A are identical. In a further embodiment, the polymerizable substituents A are different from each other.

In formula (II), A contains a polymerizable double bond. A carbonyl group may be adjacent to the double bond. Accordingly, x may be 0 or 1 and y may be 0 or 1. Two carbonyl groups adjacent to the same polymerizable double bond cannot be present in a substituent A. Accordingly, x and y cannot be both 1.

Substituent A further contains moieties L and M. L is a hydrogen atom, a C1-6 alkyl group, a C3-8 cycloalkyl group, a C6.14 aryl group or a group of formula (III). Specific examples of the C1-6 alkyl groups are methyl, ethyl, n-propyl, i-propyl, n-butyl, i-butyl or tert.-butyl. Examples of the C3-8 cycloalkyl are cyclopropyl, cyclobutyl, cyclopentyl and cyclohexyl. Specific examples of the C6-14 aryl groups are phenyl or naphtyl. The C,_6alky group, the C3-14 cycloalkyl group and the C6-14 aryl group may optionally be substituted by one or more members of the group selected from a C1-4 alkyl group, C1-4 alkoxy group, and a phenyl. Examples for a C1-4 alkyl group can include linear or branched alkyl groups having 1 to 4 carbon atoms, for example, methyl, ethyl, n-propyl, isopropyl, n-butyl, isobutyl, sec-butyl, tert-butyl. Examples for an C1-4 alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

When L is a group of formula (III) then R' is a hydrogen atom, a C1-6 alkyl group, a C3.8 cycloalkyl group, or a C6.14 aryl group. Specific examples of the C1-6 alkyl groups are methyl, ethyl, n-propyl, i-propyl, n-butyl, i-butyl or tert.-butyl. Examples of the C3.8 cycloalkyl are cyclopropyl, cyclobutyl, cyclopentyl and cyclohexyl. Specific examples of the C6.14 aryl groups are phenyl or naphtyl. The C1-6alkyl group, the C3-14 cycloalkyl group and the C6.14 aryl group may optionally be substituted by one or more members of the group selected from a C1-4 alkyl group, C1-4 alkoxy group, and a phenyl. Examples for a C1-4 alkyl group can include linear or branched alkyl groups having 1 to 4 carbon atoms, for example, methyl, ethyl, n-propyl, isopropyl, n-butyl, isobutyl, sec-butyl, tert-butyl. Examples for an C1-4 alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

When Lisa group of formula (III) then X is O, S, NH or NR" wherein R" is a C1-6 alkyl group, a C3-8 cycloalkyl group, a C6-14 aryl group. Specific examples of the C1-6 alkyl groups are methyl, ethyl, n-propyl, i-propyl, n-butyl, i-butyl or tert.-butyl. Examples of the C3-8 cycloalkyl are cyclopropyl, cyclobutyl, cyclopentyl and cyclohexyl. Specific examples of the C6-14 aryl groups are phenyl or naphtyl. The C1-6alkyl group, the C3-14 cycloalkyl group and the C6.14 aryl group may optionally be substituted by one or more members of the group selected from a C1-4 alkyl group, C1-4 alkoxy group, and a phenyl. Examples for a C1-4 alkyl group can include linear or branched alkyl groups having 1 to 4 carbon atoms, for example, methyl, ethyl, n-propyl, isopropyl, n-butyl, isobutyl, sec-butyl, tert-butyl. Examples for an C1-4 alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

When L is a group of formula (III) then a is 0 or 1.

In a group of formula (II), M is a group of formula (IV). When b, c, and d in Formula (IV) is 0 then M represents a single bond.

When M is not a single bond, then Y in formula (IV) is O, S, NH or NR'" wherein R'" is a C1-6 alkyl group, a C3-8 cycloalkyl group, a C6-14 aryl group. Specific examples of the C1-6 alkyl groups are methyl, ethyl, n-propyl, i-propyl, n-butyl, i-butyl or tert.-butyl. Examples of the C3.8 cycloalkyl are cyclopropyl, cyclobutyl, cyclopentyl and cyclohexyl. Specific examples of the C6-i4<arv>'9<r0U>P<s are> phenyl or naphtyl. The C1-6alkyl group, the C3.14 cycloalkyl group and the C6-14 aryl group may optionally be substituted by one or more members of the group selected from a C1-4 alkyl group, C1-4 alkoxy group, and a phenyl. Examples for a C1-4 alkyl group can include linear or branched alkyl groups having 1 to 4 carbon atoms, for example, methyl, ethyl, n-propyl, isopropyl, n-butyl, isobutyl, sec-butyl, tert-butyl. Examples for an C1-4 alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

When M is not a single bond, then b is an integer of from 0 to 3; c is 0 or 1; d is an integer of from 0 to 3.

In formula (IV), when b is 0 and y is 1, then Y cannot be an oxygen atom. Otherwise, the polymerizable double bond of substituent A would be linked by a hydrolysable ester bond. Furthermore, an aldehyde group cannot be adjacent to the polymerizable double bond. Accordingly, x cannot be 1 when L or a group of formula (III) is a hydrogen atom. Still further, an hetero atom such as oxygen, sulfur and nitrogen cannot be adjacent to the polymerizable double bond. Accordingly, when x is 0 then a is also 0; and when y is 0 then b is greater than 0 or c is 0.

A compound of formula (I) may contain up to 3 substituents B which may be the same or different and independently represent an acidic group. Preferably, the acidic groups are selected from a sulfonic acid group, a phosphoric acid ester group, a phosphonic acid group, and a carboxylic acid group.

The mixture of the hydrolysis-stable polymerizabe monomers of formula (I) is contained in the self-adhesive dental restorative composition in an amount of from 10 to 40 percent by weight based on the total weight of the composition. More preferably, 15 to 35 percent by weight are contained.

A preferred group of monomers of formula (I) are those, wherein n is 0, and wherein A is a moiety of formula (II) wherein L is a hydrogen atom, a C1-6 alkyl group, a C3-8 cycloalkyl group, or a C6-14 aryl group, and x is 0. More preferably, in this group A is a moiety of formula (II) wherein y is 1, and wherein M is a moiety of formula (IV) wherein Y is NH or NR'" wherein R<1>" is a C1-6 alkyl group, a C3.8 cycloalkyl group, a C6-14 aryl group, b is 0, c is 1, and d is an integer of from 0 to 3.

A further preferred group of monomers of formula (I) are those, wherein n is 0, and wherein A is a moiety of formula (II) wherein x is 1. More preferably, L is a group of formula (III) wherein R' is a C1-6 alkyl group, a C3-8 cycloalkyl group, or a C6-14 aryl group, X is O, S, NH or NR" wherein R" is a C1-6 alkyl group, a C3.8 cycloalkyl group, a C6-14 aryl group, and a is 1.

A further preferred group of monomers of formula (I) are those, wherein n is greater than 0, and wherein A is a moiety of formula (II) wherein L is a hydrogen atom, a C1-6 alkyl group, a C3_8 cycloalkyl group, or a C6-14 aryl group, and x is 0. More preferably, A is a moiety of formula (II) wherein y is 0, L is a hydrogen atom, and M is a group of formula (IV) wherein Y is O, b and c are 1, and d is an integer of from 0 to 3.

A further preferred group of monomers of formula (I) are those, wherein A is a moiety of formula (II) wherein y is 0, L is a hydrogen atom, and M is a group of formula (IV) wherein Y is NH or NR" wherein R" is a C1-6 alkyl group, a C3-8 cycloalkyl group, a C6-14 aryl group, b is 0, c is 1, and d is an integer of from 0 to 3.

The self-adhesive dental restorative composition according to the present invention contains a filler. The filler may be an inorganic or organic filler or combinations thereof. A suitable inorganic particulate filler may include fused silica, quartz, crystalline silica, amorphous silica, soda glass beads, glass rods, ceramic oxides, particulate silicate glass, radiopaque glasses (barium and strontium glasses), and synthetic minerals. It is also possible to employ finely divided materials and powdered hydroxyl-apatite, although materials that react with silane coupling agents are preferred. Also available as a filler are colloidal or submicron silicas coated with a polymer. Preferably, the filler is an inorganic filler and preferably contains a barium alumoborosilicate glass, a strontium alumino sodium fluoro phosphorosilicate glass, La2O3, ZrO2, BiPO4, CaWO4, BaWO4, SrF2, and/or Bi2O3. Suitable organic fillers include polymer granulates such as polytetrafluoroethylene particles. Small amounts of pigments to allow matching of the composition to various shades of teeth can be included. The filler particles would be generally smaller than about 5 microns in diameter and preferably smaller than 3 [mu]m, preferably in a range of from 0.1 to 1 [mu]m. The radio opacity of the cured composition of the invention is at least 3 mm/mm Al, preferably at least 5 to 7 mm/mm Al, and most preferably at least 7 mm/mm Al.

The filler is preferably contained in the dental restorative material in an amount of 60 to 90% by weight, more preferably from 70 to 85% by weight.

The self-adhesive dental restorative composition according to the present invention contains a polymerization initiator system. The initiator is not particularly limited and may be preferably a photoinitiator. Specifically, camphor quinone may be mentioned.

The self-adhesive dental restorative composition according to the invention may comprise an organic water soluble solvent and/or water. The organic water soluble solvent may be selected from alcohols, such as ethanol, propanol, butanol; and/or ketones such as acetone and methyl ethyl ketone. Particularly preferred is acetone, ethanol and/or tert-butanol. Preferably, the total amount of solvent and water in the restorative composition is in the range of from 0.5 to 20 percent by weight.

Preferably, the molecular weight of the compound of formula (I) is in the range of from 100 to 1000, more preferably up to 500.

The self-adhesive dental restorative composition according to the present invention may further contain a reactive diluent. Specific examples of a reactive diluent is selected from (meth)acrylic acid and itaconic acid.

The self-adhesive dental restorative composition according to any one of the preceding claims, which has a flexural strength of at least 90 MPa, a compressive strength of at least 300 MPa, and an adhesion to dentine of at least 3 MPa.

The self-adhesive dental restorative composition according to the invention is preferably a one-part composition. A one-part composition means that the restorative composition of the present invention is contained in only one container which may be stored and allows application of the restorative composition without any mixing and without any special equipment before the application.

A hydrolysis-stable polymerizable monomers of formula (I) may be prepared according to the methods as disclosed in WO02/13768, WO03/013444, WO03/035013; WO2004/078100, WO2005/063778, EP 05 022 930.1, and EP 06 021 540.7.

EXAMPLES

Example 1

Preparation of a One-Part Light Curing Paste for a Self-Adhesive Restorative (SAR)

The following self-adhesive composite may be prepared:

Components g wt.-%

N,N<'>-Bisacrylamid[sigma]-N,N'-diethyl-1,3-propane 33.24 11.70 3,(4),8,(9)-bis(acrylamido methyl)tricyclo-5.2.1.0<2[beta]> 16.75 5.90 decane Pentaerythritol triallyl ether monophosphate 2.85 1.00

2-Acrylamido-2-methyl-propane-sulfonic acid 1.74 0.61 tert. Butyl hydroquinone 0.016 0.006 camphor quinone 0.23 0.08

Acylphosphin oxide (L-TPO Lucirin) 0.58 0.20

4-Dimethylamino benzonitrile 0.27 0.09

Water 28.4 10.00

Strontium alumo flouro silicate glass 200.0 70.41

TOTAL 284 100

The self-adhesive composite shows a flexural strength of at least 90 MPa, a compressive strength of at least 300 MPa, and an adhesion to dentine of at least 3 MPa.

The invention claimed is:

1. Self-adhesive dental restorative composition comprising (i) 10 to 40 percent by weight based on the total weight of the composition of a mixture of hydrolysis stable polymerizable monomers of the following formula (I):

$$R(A)_m(B)_n \quad (I)$$

wherein

R is a m+n valent organic group having 1 to 20 carbon atoms and optionally 1 to 5 atoms selected from the group of nitrogen, oxygen and sulfur atoms;

A independently represents a moiety of the following formula (II):

(II)

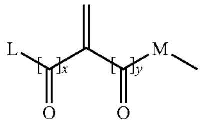

wherein

L is a hydrogen atom, a $C_{1-6}$ alkyl group, a $C_{3-8}$ cycloalkyl group, a $C_{6-14}$ aryl group or a group of the following formula (III):

(III)

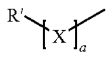

wherein

R' is a hydrogen atom, a $C_{1-6}$ alkyl group, a $C_{3-8}$ cycloalkyl group, or a $C_{6-14}$ aryl group;

X is O, S, NH or NR" wherein R" is a $C_{1-6}$ alkyl group, a $C_{3-8}$ cycloalkyl group, or a $C_{6-14}$ aryl group;

a is 0 or 1;

M is a group of the following formula (IV)

(IV)

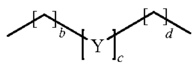

wherein

Y is O, Si NH or NR"' wherein R"' is a $C_{1-6}$ alkyl group, a $C_{3-8}$ cycloalkyl group, or a $C_{6-14}$ aryl group;

b is an integer of from 0 to 3;

c is 0 or 1;

d is an integer of from 0 to 3;

provided that when b is 0, then Y cannot be 0;

x is 0 or 1;

y is 0 or 1;

provided that x and y cannot be both 1, and provided that x cannot be 1 when L or a group of formula (III) is a hydrogen atom, and provided that when x is 0 then a is also 0, and provided that when y is 0 then b is greater than 0 or c is 0;

B independently represents an acidic group;

m is an integer of from 1 to 5;

n is an integer of 0 to 3; and m+n is at least 2;

(ii) 60 to 90 percent by weight based on the total weight of the composition of a filler;

(iii) an initiator system; and (iv) a reactive diluent selected from the group consisting of (meth) acrylic acid and itaconic acid;

wherein the portion of monomers of formula (I) with n greater than 0 is at least 1 percent by weight based on the total weight of the mixture.

2. The self-adhesive dental restorative composition according to claim 1, wherein B is selected from a sulfonic acid group, a phosphoric acid ester group, a phosphonic acid group, and a carboxylic acid group.

3. The self-adhesive dental restorative composition according to claim 1, wherein R is a m+n valent organic group having 1 to 6 carbon atoms.

4. The self-adhesive dental restorative composition according to claim 1, wherein n is 0, and wherein A is a moiety of formula (II) wherein L is a hydrogen atom, a $C_{1-5}$ alkyl group, a $C_{3-8}$ cycloalkyl group, or a $C_{5-14}$ aryl group, and x is 0.

5. The self-adhesive dental restorative composition according to claim 4, wherein A is a moiety of formula (II) wherein y is 1, and wherein M is a moiety of formula (IV) wherein Y is NH or NR''' wherein R''' is a $C_{1-6}$ alkyl group, a $C_{3-8}$ cycloalkyl group, or a $C_{6-14}$ aryl group, b is 0, c is 1, and d is an integer of from 0 to 3.

6. The self-adhesive dental restorative composition according to claim 1, wherein n is 0, and wherein A is a moiety of formula (II) wherein x is 1.

7. The self-adhesive dental restorative composition according to claim 6, wherein L is a group of formula (III) wherein R' is a $C_{1-6}$ alkyl group, a $C_{3-8}$ cycloalkyl group, or a $C_{6-14}$ aryl group, X is O, S, NH or NR'' wherein R'' is a $C_{1-6}$ alkyl group, a $C_{3-8}$ cycloalkyl group, or a $C_{6-14}$ aryl group, and a is 1.

8. The self-adhesive dental restorative composition according to claim 1, wherein n is greater than 0, and wherein A is a moiety of formula (II) wherein L is a hydrogen atom, a $C_{1-6}$ alkyl group, a $C_{3-8}$ cycloalkyl group, or a $C_{6-14}$ aryl group, and x is 0.

9. The self-adhesive dental restorative composition according to claim 8, wherein A is a moiety of formula (II) wherein y is 0, L is a hydrogen atom, and M is a group of formula (IV) wherein Y is 0, b and c are 1, and d is an integer of from 0 to 3.

10. The self-adhesive dental restorative composition according to claim 8, wherein A is a moiety of formula (II) wherein y is 0, L is a hydrogen atom, and M is a group of formula (IV) wherein Y is NH or NR'' wherein R'' is a $C_{1-6}$ alkyl group, a $C_{3-8}$ cycloalkyl group, or a $C_{6-14}$ aryl group, b is 0, c is 1, and d is an integer of from 0 to 3.

11. The self-adhesive dental restorative composition according to claim 1, wherein the filler is an inorganic filler comprising a barium alumoborosilicate glass, a strontium alumino sodium fluoro phosphorosilicate glass, $La_2O_3$, $ZrO_2$, $BiPO_4$, $CaWO_4$, $BaWO_4$, $SrF_2$, and/or $Bi_2O_3$.

12. The self-adhesive dental restorative composition according to claim 1, further comprising water.

13. The self-adhesive dental restorative composition according to claim 1, wherein the molecular weight of the compound of formula (I) is in the range of from 100 to 1000.

14. The self-adhesive dental restorative composition according to claim 1, which has a flexural strength of at least 90 MPa, a compressive strength of at least 300 MPa, and an adhesion to dentine of at least 3 MPa.

15. The self-adhesive dental restorative composition according to claim 1, which is a one-part composition.

16. The self-adhesive dental restorative composition according to claim 1, which is a self-adhesive dental composite, a filler containing self-adhesive sealer or a self-adhesive cement.

17. A process for the preparation of a self-adhesive dental restorative composition comprising the step of mixing (i) 10 to 40 percent by weight based on the total weight of the composition of a mixture of hydrolysis-stable polymerizable monomers of the following formula (I):

$$R(A)_m(B)_n \quad (I)$$

wherein

R is a m+n valent organic group having 1 to 20 carbon atoms and optionally 1 to 5 atoms selected from the group of nitrogen, oxygen and sulfur atoms;

A independently represents a moiety of the following formula (II):

(II)

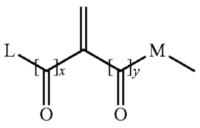

wherein

L is a hydrogen atom, a $C_{1-6}$ alkyl group, a $C_{3-8}$ cycloalkyl group, a $C_{6-14}$ aryl group or a group of the following formula (III)

(III)

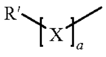

wherein

R' is a hydrogen atom, a $C_{1-6}$ alkyl group, a $C_{3-8}$ cycloalkyl group, or a $C_{6-14}$ aryl group;

X is O, S, NH or NR'' wherein R'' is a $C_{1-6}$ alkyl group, a $C_{3-8}$ cycloalkyl group, or a $C_{6-14}$ aryl group;

a is 0 or 1;

M is a group of the following formula (IV)

(IV)

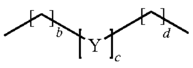

wherein

Y is O, S, NH or NR''' wherein R''' is a $C_{1-6}$ alkyl group, a $C_{3-8}$ cycloalkyl group, or a $C_{6-14}$ aryl group;

b is an integer of from 0 to 3;
c is 0 or 1;
d is an integer of from 0 to 3;
provided that when b is 0, then Y cannot be 0;
x is 0 or 1;
y is 0 or 1;
provided that x and y cannot be both 1, and
provided that x cannot be 1 when L or a group of formula (III) is a hydrogen atom, and
provided that when x is 0 then a is also 0, and provided that when y is 0 then b is greater than 0 or c is 0;

B independently represents an acidic group;
m is an integer of from 1 to 5;
n is an integer of 0 to 3; and
m+n is at least 2;

(ii) 60 to 90 percent by weight based on the total weight of the composition of a filler;
(iii) an initiator system; and
(iv) a reactive diluent selected from the group consisting of (meth) acrylic acid and itaconic acid;

wherein the portion of monomers of formula (I) with n greater than 0 is at least 1 percent by weight based on the total weight of the mixture.

* * * * *